(12) United States Patent
Ryu

(10) Patent No.: US 9,778,396 B2
(45) Date of Patent: Oct. 3, 2017

(54) POLYMERIZABLE COMPOSITION FOR OPTICAL MATERIAL, OPTICAL MATERIAL OBTAINED FROM SAME COMPOSITION, AND PLASTIC LENS

(71) Applicant: MITSUI CHEMICALS, INC., Minato-ku (JP)

(72) Inventor: Akinori Ryu, Arao (JP)

(73) Assignee: MITSUI CHEMICALS, INC., Tokyo (JP)

( * ) Notice: Subject to any disclaimer, the term of this patent is extended or adjusted under 35 U.S.C. 154(b) by 239 days.

(21) Appl. No.: 14/406,963

(22) PCT Filed: Jun. 19, 2013

(86) PCT No.: PCT/JP2013/066812
§ 371 (c)(1),
(2) Date: Dec. 10, 2014

(87) PCT Pub. No.: WO2014/002844
PCT Pub. Date: Jan. 3, 2014

(65) Prior Publication Data
US 2015/0177416 A1  Jun. 25, 2015

(30) Foreign Application Priority Data

Jun. 26, 2012  (JP) .................................. 2012-143125

(51) Int. Cl.
| | |
|---|---|
| C08K 5/16 | (2006.01) |
| G02B 1/04 | (2006.01) |
| C08G 18/73 | (2006.01) |
| C08G 18/75 | (2006.01) |
| C08G 18/76 | (2006.01) |
| C08G 18/38 | (2006.01) |
| B29C 39/00 | (2006.01) |
| B29C 39/02 | (2006.01) |
| C08G 18/72 | (2006.01) |
| G02B 5/23 | (2006.01) |
| C07D 493/04 | (2006.01) |
| C09K 9/02 | (2006.01) |
| G02C 7/10 | (2006.01) |
| B29L 11/00 | (2006.01) |

(52) U.S. Cl.
CPC ............ *G02B 1/041* (2013.01); *B29C 39/006* (2013.01); *B29C 39/02* (2013.01); *C07D 493/04* (2013.01); *C08G 18/38* (2013.01); *C08G 18/3876* (2013.01); *C08G 18/72* (2013.01); *C08G 18/73* (2013.01); *C08G 18/755* (2013.01); *C08G 18/758* (2013.01); *C08G 18/7642* (2013.01); *G02B 1/04* (2013.01); *G02B 5/23* (2013.01); *B29L 2011/00* (2013.01); *C09K 9/02* (2013.01); *G02C 7/10* (2013.01)

(58) Field of Classification Search
CPC ........ C08K 6/1545; G02B 1/04; G02B 1/041; C09K 9/02; G02C 7/10; G02C 7/102
USPC .......................................................... 524/717
See application file for complete search history.

(56) References Cited

U.S. PATENT DOCUMENTS

| | | | |
|---|---|---|---|
| 4,889,413 A | 12/1989 | Ormsby et al. | |
| 5,679,756 A * | 10/1997 | Zhu ........................ | C08G 18/10 525/451 |
| 5,693,738 A * | 12/1997 | Okazaki ............. | C08G 18/1875 264/1.1 |
| 5,851,593 A | 12/1998 | Jones | |
| 6,107,395 A | 8/2000 | Rosthauser et al. | |
| 6,187,444 B1 | 2/2001 | Bowles, III et al. | |
| 6,506,538 B1 | 1/2003 | Breyne et al. | |
| 7,214,754 B2 | 5/2007 | Nagpal | |
| 7,332,260 B2 | 2/2008 | Breyne et al. | |
| 8,486,312 B2 | 7/2013 | Melzig et al. | |
| 2002/0197562 A1* | 12/2002 | Breyne ................ | C07D 311/78 430/270.15 |
| 2008/0036964 A1* | 2/2008 | Miura ................ | B29D 11/0073 351/159.27 |
| 2010/0249264 A1 | 9/2010 | Hu et al. | |
| 2013/0273380 A1* | 10/2013 | Hickenboth .............. | C08F 4/32 428/446 |
| 2013/0274412 A1* | 10/2013 | Hickenboth ......... | C08G 18/671 524/606 |
| 2015/0301227 A1* | 10/2015 | Ryu ........................ | C09K 9/02 351/159.61 |
| 2016/0170107 A1* | 6/2016 | Ryu ........................ | C09K 9/02 252/586 |

FOREIGN PATENT DOCUMENTS

| | | |
|---|---|---|
| JP | 8-272036 A | 10/1996 |
| JP | 2004-500319 A | 1/2004 |
| JP | 2004-078052 A | 3/2004 |

(Continued)

OTHER PUBLICATIONS

Machine translation of JP 2004-078052 A, Kuwata et al., published Mar. 11, 2004.*
Extended Search Report issued by the European Patent Office in corresponding European Patent Application No. 13809622.7 on Nov. 18, 2015 (5 pages).

(Continued)

Primary Examiner — Jane L Stanley
(74) Attorney, Agent, or Firm — Buchanan, Ingersoll & Rooney PC

(57) ABSTRACT

A polymerizable composition for an optical material includes (A) one or more isocyanate compounds selected from aliphatic isocyanate compounds and alicyclic isocyanate compounds, (B) an active hydrogen compound having two or more functional groups, and (C) a photochromic compound.

8 Claims, No Drawings

(56) References Cited

FOREIGN PATENT DOCUMENTS

| JP | 2005-023238 A | 1/2005 |
| JP | 2005-305306 A | 11/2005 |
| JP | 2006-509097 A | 3/2006 |
| JP | 2007-525462 A | 9/2007 |
| JP | 2008-030439 A | 2/2008 |
| JP | 2011-518849 A | 6/2011 |
| JP | 2011-144181 A | 7/2011 |
| WO | WO 00/15628 A1 | 3/2000 |
| WO | WO 2004/063236 A1 | 7/2004 |
| WO | WO 2004/099172 A1 | 11/2004 |

OTHER PUBLICATIONS

International Search Report (PCT/ISA/210) mailed on Sep. 17, 2013, by the Japanese Patent Office as the International Searching Authority for International Application No. PCT/JP2013/066812.
Office Action issued by the Japanese Patent Office in corresponding Japanese Patent Application No. 2014-522565 on Jan. 12, 2016 (2 pages).

* cited by examiner

POLYMERIZABLE COMPOSITION FOR OPTICAL MATERIAL, OPTICAL MATERIAL OBTAINED FROM SAME COMPOSITION, AND PLASTIC LENS

TECHNICAL FIELD

The present invention relates to a polymerizable composition for an optical material including a photochromic compound, an optical material obtained from the same composition, and a plastic lens.

BACKGROUND ART

Due to its lighter weight and better crack resistance compared with an inorganic lens, a plastic lens is rapidly being distributed as an optical element such as an eyeglasses lens or a camera lens. In recent years, development of a plastic lens having photochromic performance has been in progress.

Examples of the above-described plastic lens include techniques described in Patent Documents 1 to 4.

Patent Document 1 describes a lens comprised of a composition including a predetermined photochromic compound and a di(meth)acrylate compound. Paragraph [0009] describes that, in a case in which a urethane resin or a thiourethane resin having a high refractive index is used, isocyanate that is a raw material of the resin reacts with the photochromic compound in a monomer phase, and the photochromic performance is no longer exhibited.

Patent Document 2 discloses a lens in which a coating layer comprised of a composition including a photochromic compound having a chromene skeleton and a phenol compound is provided on the surface of a thiourethane-based plastic lens.

Patent Document 3 discloses a photochromic lens including a lens base material comprised of a thiourethane resin and a photochromic film formed by applying a solution including a photochromic compound and a radical polymerizable monomer onto the base material.

Meanwhile, Patent Document 4 discloses a compound having photochromic characteristics.

RELATED DOCUMENT

Patent Document

[Patent Document 1] Japanese Unexamined Patent Publication No. H8-272036
[Patent Document 2] Japanese Unexamined Patent Publication No. 2005-23238
[Patent Document 3] Japanese Unexamined Patent Publication No. 2008-30439
[Patent Document 4] Japanese Unexamined Patent Publication No. 2011-144181
[Patent Document 5] U.S. Pat. No. 6,506,538
[Patent Document 6] Japanese Unexamined Patent Publication No. 2005-305306

DISCLOSURE OF THE INVENTION

However, the inventions described in the above-described documents had the following problems.

The photochromic lenses described in Patent Documents 1 to 3 had the photochromic film provided on the base material comprised of a urethane resin or a thiourethane resin. As described in Paragraph [0009] in Patent Document 1, the photochromic compound reacted with isocyanate that was a monomer, and the photochromic performance became fully lost.

To obtain a lens having the above-described configuration, it was necessary to provide a photochromic film on the lens base material, and therefore the manufacturing steps became troublesome, and there was room for the improvement of manufacturing stability. In addition, since the lens had a laminate structure, there were problems of peeling at interfaces, the adjustment of the refractive index, and the like, and thus there was a possibility that the yield of products might decrease.

The invention can be as described below.

[1] A polymerizable composition for an optical material including:

(A) one or more isocyanate compounds selected from aliphatic isocyanate compounds and alicyclic isocyanate compounds;

(B) an active hydrogen compound having two or more functional groups; and (C) a photochromic compound.

[2] The polymerizable composition for an optical material according to [1], wherein the photochromic compound (C) is represented by the following formula (3),

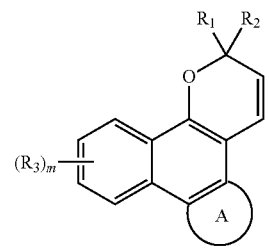

(3)

wherein in the formula, $R_1$ and $R_2$ may be identical or different, and independently represent a hydrogen atom;

a linear or branched alkyl group having 1 to 12 carbon atoms;

a cycloalkyl group having 3 to 12 carbon atoms;

a substituted or unsubstituted aryl group having 6 to 24 carbon atoms or a substituted or unsubstituted heteroaryl group having 4 to 24 carbon atoms in which these substituted groups, as a substituent, include at least one substituent selected from a halogen atom, a hydroxyl group, a linear or branched alkyl group having 1 to 12 carbon atoms, a linear or branched alkoxy group having 1 to 12 carbon atoms, a linear or branched haloalkyl group having 1 to 12 carbon atoms that is substituted by at least one halogen atom, a linear or branched haloalkoxy group having 1 to 12 carbon atoms that is substituted by at least one halogen atom, a phenoxy group or naphthoxy group substituted by at least one linear or branched alkyl group or alkoxy group having 1 to 12 carbon atoms, a linear or branched alkenyl group having 2 to 12 carbon atoms, a —$NH_2$ group, a —NHR group, a —$N(R)_2$ group in which R represents a linear or branched alkyl group having 1 to 6 carbon atoms, in which in a case that two Rs are present, the two Rs may be identical or different, a methacryloyl group and an acryloyl group; or an aralkyl or heteroaralkyl group that a linear or branched alkyl group having 1 to 4 carbon atoms is substituted by the aryl group or the heteroaryl group, $R_3$ may be identical or different, and independently represent a halogen atom;

a linear or branched alkyl group having 1 to 12 carbon atoms;

a cycloalkyl group having 3 to 12 carbon atoms;

a linear or branched alkoxy group having 1 to 12 carbon atoms;

a linear or branched haloalkyl group having 1 to 12 carbon atoms that is substituted by at least one halogen atom, a halocycloalkyl group having 3 to 12 carbon atoms that is substituted by at least one halogen atom, a linear or branched haloalkoxy group having 1 to 12 carbon atoms that is substituted by at least one halogen atom;

a substituted or unsubstituted aryl group having 6 to 24 carbon atoms or a substituted or unsubstituted heteroaryl group having 4 to 24 carbon atoms in which these substituted groups, as a substituent, include at least one substituent selected from a halogen atom, a hydroxyl group, a linear or branched alkyl group having 1 to 12 carbon atoms, a linear or branched alkoxy group having 1 to 12 carbon atoms, a linear or branched haloalkyl group having 1 to 12 carbon atoms that is substituted by at least one halogen atom, a linear or branched haloalkoxy group having 1 to 12 carbon atoms that is substituted by at least one halogen atom, a phenoxy group or naphthoxy group substituted by at least one linear or branched alkyl group or alkoxy group having 1 to 12 carbon atoms, a linear or branched alkenyl group having 2 to 12 carbon atoms, and an amino group;

an aralkyl or heteroaralkyl group that a linear or branched alkyl group having 1 to 4 carbon atoms is substituted by the aryl group or heteroaryl group;

a substituted or unsubstituted phenoxy group or naphthoxy group, in which these substituted groups, as a substituent, include at least one substituent selected from a linear or branched alkyl group or alkoxy group having 1 to 6 carbon atoms;

—$NH_2$, —NHR, —$CONH_2$, or —CONHR in which R represents a linear or branched alkyl group having 1 to 6 carbon atoms; or —$OCOR_8$ or —$COOR_8$ in which $R_8$ represents a linear or branched alkyl group having 1 to 6 carbon atoms, a cycloalkyl group having 3 to 6 carbon atoms, or a phenyl group substituted by at least one substituents of the substituted aryl and the substituted heteroaryl group of $R_1$ or $R_2$, or an unsubstituted phenyl group;

m is an integer of 0 to 4;

A represents an annelated ring of the following formula ($A_2$) or formula ($A_4$), ($A_2$)

($A_4$)

wherein, in the annelated ring, the dotted lines represent a chemical bond between a carbon $C_5$ and a carbon $C_6$ in a naphthopyran ring of a formula (3);

an α bond in the annelated ring ($A_4$) can be bonded with the carbon $C_5$ or the carbon $C_6$ in the naphthopyran ring of Formula (3) in an ordinary manner;

$R_4$ is identical or different, and independently represents OH, a linear or branched alkyl group or alkoxy group having 1 to 6 carbon atoms; two $R_4$s form carbonyl (CO);

$R_5$ represents halogen atom;

a linear or branched alkyl group having 1 to 12 carbon atoms;

a linear or branched haloalkyl group having 1 to 6 carbon atoms that is substituted by at least one halogen atom;

a cycloalkyl group having 3 to 12 carbon atoms;

a linear or branched alkoxy group having 1 to 6 carbon atoms;

a substituted or unsubstituted phenyl or benzyl group in which these substituted groups include at least one substituents described in the definition of the $R_1$ and $R_2$ groups as a substituent in a case that $R_1$ and $R_2$ in Formula (3) independently correspond to an aryl or heteroaryl group;

—$NH_2$ or —NHR in which R represents a linear or branched alkyl group having 1 to 6 carbon atoms;

a substituted or unsubstituted phenoxy group or naphthoxy group in which these substituted groups, as a substituent, include at least one substituent selected from a linear or branched alkyl group or alkoxy group having 1 to 6 carbon atoms; or a —$COR_9$, —$COOR_9$, or —$CONHR_9$ group in which $R_9$ represents a linear or branched alkyl group having 1 to 6 carbon atoms, a cycloalkyl group having 3 to 6 carbon atoms, or a substituted or unsubstituted phenyl or benzyl group in which substituents of these substituted groups include at least one substituents described in the definition of the $R_1$ and $R_2$ groups as a substituent in a case that $R_1$ and $R_2$ in Formula (3) independently correspond to an aryl or heteroaryl group, in a case in which A represents ($A_4$), n is an integer of 0 to 2, p is an integer of 0 to 4, and in a case in which A represents ($A_2$), n is an integer of 0 to 2.

[3] The polymerizable composition for an optical material according to [1] or [2], in which the isocyanate compound (A) is one or more selected from a group consisting of 1,6-hexamethylene diisocyanate, 2,5-bis(isocyanatomethyl)bicyclo-[2.2.1]-heptane, 2,6-bis(isocyanatomethyl)bicyclo-[2.2.1]-heptane, isophorone diisocyanate, and compounds represented by the following formula (1)

(1)

(In Formula (1), $Q_1$ and $Q_2$ may be identical or different, and represent a hydrogen atom or an alkyl group having 1 to 6 carbon atoms. $X_1$ and $X_2$ may be identical or different, and represent a hydrogen atom or an alkyl group having 1 to 6 carbon atoms.).

[4] The polymerizable composition for an optical material according to [3], in which the isocyanate compound (A) includes the compound represented by Formula (1).

[5] The polymerizable composition for an optical material according to any one of [1] to [4], in which the alicyclic isocyanate compound is bis(isocyanatocyclohexyl)methane.

[6] The polymerizable composition for an optical material according to any one of [1] to [5], in which the active hydrogen compound (B) is one or more selected from a group consisting of polyol compounds, polythiol compounds, and thiol compounds having a hydroxyl group.

[7] The polymerizable composition for an optical material according to any one of [1] to [6], in which the active hydrogen compound (B) is one or more selected from a group consisting of pentaerythritol tetrakis(2-mercaptoacetate), pentaerythritol tetrakis(3-mercaptopropionate), bis(mercaptoethyl) sulfide, 4-mercaptomethyl-1,8-dimercapto-3,6-dithiaoctane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, 2,5-dimercapto-1,4-dithiane, 1,1,3,3-tetrakis(mercaptomethylthio) propane, 4,6-bis(mercaptomethylthio)-1,3-dithiane, 2-(2,2-bis(mercaptomethylthio)ethyl)-1,3-dithietane, trimethylolpropane tris(3-mercaptopropionate), and compounds represented by Formula (2)

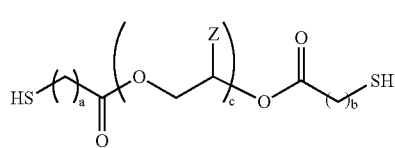

(2)

(in the formula, a and b independently represent an integer of 1 to 4, and c represents an integer of 1 to 3. Z is hydrogen or a methyl group, and in a case in which a plurality of Zs is present, Zs may be identical or different, respectively.)

[8] An optical material comprised of the polymerizable composition according to any one of [1] to [7].

[9] A plastic lens including a base material comprised of the polymerizable composition according to any one of [1] to [7].

[10] A method for manufacturing a plastic lens including: a step of mixing (A) one or more isocyanate compounds selected from aliphatic isocyanate compounds and alicyclic isocyanate compounds, (B) an active hydrogen compound having two or more functional groups, and (C) a photochromic compound in one batch to prepare a polymerizable composition for an optical material; and a step of forming a lens base material by polymerizing the polymerizable composition for an optical material using a mold.

According to the polymerizable composition for an optical material of the invention, it is possible to obtain a urethane resin-based optical material or a thiourethane resin-based optical material and a plastic lens including a photochromic compound using an aliphatic or alicyclic isocyanate without causing the performance degradation of the photochromic compound.

DESCRIPTION OF EMBODIMENTS

A polymerizable composition for an optical material of the invention will be described on the basis of the following embodiments.

A polymerizable composition for an optical material of the present embodiment includes (A) one or more isocyanate compounds selected from aliphatic isocyanate compounds and alicyclic isocyanate compounds, (B) an active hydrogen compound having two or more functional groups, and (C) a photochromic compound.

When a specific isocyanate compound (A) and a specific photochromic compound (C) are used, the polymerizable composition for an optical material of the embodiment is capable of exhibiting photochromic performance in a urethane resin-based optical material or a thiourethane resin-based optical material as well.

Hereinafter, the respective components will be described.

[(A) Isocyanate Compound]

The isocyanate compound (A) in the embodiment is one or more isocyanate compounds selected from aliphatic isocyanate compounds and alicyclic isocyanate compounds having 2 to 25 carbon atoms. Meanwhile, in the embodiment, isocyanate compounds having an aromatic ring in a part do not belong to the aliphatic isocyanate.

Examples of the aliphatic isocyanate compounds include 1,6-hexamethylene diisocyanate, 1,5-pentamethylene diisocyanate, 1,8-octamethylene diisocyanate, and the like, and it is also possible to use a combination including at least one of the aliphatic isocyanate compounds.

Examples of the alicyclic isocyanate compounds include compounds represented by the following formula (1), 2,5-bis(isocyanatomethyl) bicyclo-[2.2.1]-heptane, 2,6-bis(isocyanatomethyl)bicyclo-[2.2.1]-heptane, 1,3-bis(isocyanatomethyl)cyclohexane, 1,4-bis(isocyanatomethyl)cyclohexane, isophorone diisocyanate, and the like, and it is also possible to use a combination including at least one of the alicyclic isocyanate compounds.

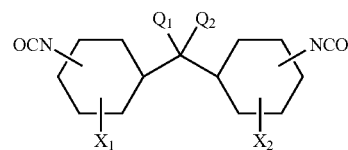

(1)

In Formula (1), $Q_1$ and $Q_2$ may be identical or different, and represent a hydrogen atom or an alkyl group having 1 to 6 carbon atoms. In the embodiment, $Q_1$ and $Q_2$ are preferably hydrogen atom.

In the formula, $X_1$ and $X_2$ may be identical or different, and represent a hydrogen atom or an alkyl group having 1 to 6 carbon atoms. In the embodiment, $X_1$ and $X_2$ are preferably a hydrogen atom.

Examples of the compound represented by Formula (1) include bis(isocyanatocyclohexyl)methane.

In the embodiment, as the isocynate compound (A), it is preferable to use at least one selected from 1,6-hexamethylene diisocyanate, compounds represented by Formula (1), isophorone diisocyanate, and 2,5(6)-bis(isocyanatomethyl)-bicyclo[2,2,1]heptane.

The isocynate compound (A) is preferably an alicyclic isocyanate compound, and, among the alicyclic isocyanate compounds, at least one selected from the compound represented by Formula (1), isophorone diisocyanate and 2,5(6)-bis(isocyanatomethyl)-bicyclo[2,2,1]heptane is more preferred, and bis(isocyanatocyclohexyl)methane, which is the compound represented by Formula (1), is particularly preferred.

When the above-described compound is used, it is possible to provide a urethane resin-based optical material or a thiourethane resin-based optical material and a plastic lens including a photochromic compound.

In the embodiment, when one or more isocynate compounds selected from the aliphatic isocyanate compounds and the alicyclic isocyanate compounds, particularly, the above-described specific isocyanate is used, it is possible to suppress a reaction between the isocyanate compound and the photochromic compound, and to maintain the performance of the photochromic compound. This is assumed to be because the solubility of the photochromic compound is low in the specific isocyanate.

[(B) an Active Hydrogen Compound Having Two or More Functional Groups]

The active hydrogen compound having two or more functional groups (B) is not particularly limited, and examples thereof include polyol compounds, polythiol compounds, thiol compounds having a hydroxyl group, and the like, and an appropriate combination thereof can be used.

Examples of the polyol compounds include aliphatic polyols such as ethylene glycol, diethylene glycol, propylene glycol, dipropylene glycol, triethylene glycol, butylene glycol, neopentyl glycol, glycerin, trimethylol ethane, trimethylol propane, di-trimethylol propane, butane triol, 1,2-methyl glucoside, pentaerythritol, dipentaerythritol, tripentaerythritol, sorbitol, erythritol, threitol, ribitol, arabinitol, xylitol, allitol, mannitol, dulcitol, iditol, glycol, inositol, hexane triol, triglycellose, diglyperol, triethylene glycol, polyethylene glycol, tris(2-hydroxyethyl) isocyanurate, cyclobutanediol, cyclopentanediol, cyclohexanediol, cycloheptanediol, cyclooctanediol, cyclohexanedimethanol, hydroxypropyl cyclohexanol, tricyclo[5.2.1.0$^{2,6}$]decane-dimethanol, bicyclo[4,3,0]-nonanediol, dicyclohexanediol, tricyclo[5,3,1,1]dodecanediol, bicyclo[4,3,0]nonane dimethanol, tricyclo[5,3,1,1]dodecane-diethanol, hydroxypropyl tricyclo[5,3,1,1]dodecanol, spiro[3,4]octanediol, butyl cyclohexanediol, 1,1'-bicyclohexylidenediol, cyclohexanetriol, maltitol, and lactose;

aromatic polyols such as dihydroxynaphthalene, trihydroxynaphthalene, tetrahydroxynaphthalene, dihydroxybenzene, benzenetriol, biphenyltetraol, pyrogallol, (hydroxynaphthyl)pyrogallol, trihydroxyphenanthrene, bisphenol A, bisphenol F, xylylene glycol, di(2-hydroxyethoxy)benzene, bisphenol A-bis-(2-hydroxyethyl ether), tetrabromobisphenol A, and tetrabromobisphenol A-bis(2-hydroxyethyl ether);

halogenated polyols such as dibromoneopentyl glycol; and high molecular polyols such as epoxy resins. In the embodiment, a combination including at least one selected from the above-described polyol compounds can be used.

Furthermore, additionally, examples of the polyol compounds include condensation reaction products between an organic acid such as oxalic acid, glutamic acid, adipic acid, acetic acid, propionic acid, cyclohexanecarboxylic acid, β-oxocyclohexanepropionic acid, dimer acid, phthalic acid, isophthalic acid, salicylic acid, 3-bromopropionic acid, 2-bromoglycolic acid, dicarboxycyclohexane, pyromellitic acid, butanetetracarboxylic acid, or bromophthalic acid and the polyol;

addition reaction products between the polyol and an alkylene oxide such as ethylene oxide or propylene oxide;

Addition reaction products between alkylenepolyamine and alkylene oxide such as ethylene oxide or propylene oxide; furthermore bis[4-(hydroxyethoxy)phenyl]sulfide, bis[4-(2-hydroxypropoxyl)phenyl]sulfide, bis[4-(2,3-dihydroxypropoxy)phenyl]sulfide, bis[4-(4-hydroxycyclohexyloxyl)phenyl]sulfide, bis[2-methyl-4-(hydroxyethoxy)-6-butylphenyl]sulfide, compounds obtained by adding ethylene oxide and/or propylene oxide having an average of three or less molecules per hydroxyl group to the above-described compounds;

polyols containing a sulfur atom such as di-(2-hydroxyethyl)sulfide, 1,2-bis(2-hydroxyethylmercapto)ethane, bis(2-hydroxyethyl)disulfide, 1,4-dithian-2,5-diol, bis(2,3-dihydroxypropyl)sulfide, tetrakis(4-hydroxy-2-thiabutyl) methane, bis(4-hydroxyphenyl)sulfone (trade name: BISPHENOL S), tetrabromobisphenol S, tetramethylbisphenol S, 4,4'-thiobis(6-tert-butyl-3-methylphenol), and 1,3-bis(2-hydroxyethylthioethyl)-cyclohexane; and the like. In the embodiment, a combination including at least one selected from the above-described polyol compounds can be used.

Examples of the polythiol compound include aliphatic polythiols such as methanedithiol, 1,2-ethanedithiol, 1,2,3-propanetrithiol, 1,2-cyclohexanedithiol, bis(2-mercaptoethyl)ether, tetrakis(mercaptomethyl)methane, diethylene glycol bis(2-mercaptoacetate), diethylene glycol bis(3-mercaptopropionate), ethylene glycol bis(2-mercaptoacetate), ethylene glycol bis(3-mercaptopropionate), trimethylolpropane tris(2-mercapto acetate), trimethylolpropane tris(3-mercaptopropionate), trimethylolethane tris(2-mercaptoacetate), trimethylolethane tris(3-mercaptopropionate), pentaerythritol tetrakis(2-mercaptoacetate), pentaerythritol tetrakis(3-mercaptopropionate), bis(mercaptomethyl)sulfide, bis(mercaptomethyl)disulfide, bis(mercaptoethyl)sulfide, bis(mercaptoethyl)disulfide, bis(mercaptopropyl)sulfide, bis(mercapto methylthio)methane, bis(2-mercaptoethylthio)methane, bis(3-mercaptopropylthio)methane, 1,2-bis(mercaptomethylthio)ethane, 1,2-bis(2-mercaptoethylthio)ethane, 1,2-bis(3-mercaptopropylthio)ethane, 1,2,3-tris(mercaptomethylthio)propane, 1,2,3-tris(2-mercaptoethylthio)propane, 1,2,3-tris(3-mercaptopropylthio)propane, 4-mercaptomethyl-1,8-dimercapto-3,6-dithiaoctane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, tetrakis(mercaptomethylthio)methane, tetrakis(2-mercaptoethylthiomethyl)methane, tetrakis(3-mercaptopropylthiomethyl)methane, bis(2,3-dimercaptopropyl)sulfide, 2,5-dimercaptomethyl-1,4-dithiane, 2,5-dimercapto-1,4-dithiane, 2,5-dimercaptomethyl-2,5-dimethyl-1,4-dithiane, esters of these compound a with thioglycolic acid or mercaptopropionic acid, hydroxymethyl sulfide bis(2-mercaptoacetate), hydroxyethyl sulfide bis(3-mercaptopropionate), hydroxyethyl disulfide bis(2-mercaptoacetate), hydroxyethyl disulfide bis(3-mercaptopropionate), hydroxymethyl disulfide bis(2-mercaptoacetate), hydroxymethyl disulfide bis(3-mercaptopropionate), hydroxyethyl disulfide bis(2-mercaptoacetate), hydroxyethyl disulfide bis(3-mercaptopropionate), 2-mercaptoethyl ether bis(2-mercaptoacetate), 2-mercaptoethyl ether bis(3-mercapto propionate), thiodiglycolic acid bis(2-mercaptoethyl ester), thiodipropionic acid bis(2-mercaptoethyl ester), dithiodiglycolic acid bis(2-mercapto ethyl ester), dithiodipropionic acid bis(2-mercapto ethyl ester), 1,1,3,3-tetrakis(mercaptomethylthio)propane, 1,1,2,2-tetrakis(mercaptomethylthio)ethane, 4,6-bis(mercaptomethylthio)-1,3-dithiane, tris(mercaptomethylthio)methane, and tris(mercaptoethylthio)methane;

aromatic polythiol compounds such as 1,2-dimercaptobenzene, 1,3-dimercaptobenzene, 1,4-dimercaptobenzene, 1,2-bis(mercapto methyl)benzene, 1,3-bis(mercapto methyl) benzene, 1,4-bis(mercapto methyl)benzene, 1,2-bis(mercapto ethyl)benzene, 1,3-bis(mercapto ethyl)benzene, 1,4-bis(mercapto ethyl)benzene, 1,3,5-trimercaptobenzene, 1,3,5-tris(mercapto methyl)benzene, 1,3,5-tris(mercapto methyleneoxy)benzene, 1,3,5-tris(mercapto ethyleneoxy) benzene, 2,5-toluenedithiol, 3,4-toluenedithiol, 1,5-naphthalene dithiol, and 2,6-naphthalene dithiol;

heterocyclic polythiol compounds such as 2-methylamino-4,6-dithol-sym-triazine, 3,4-thiophenedithiol, bismuthiol, 4,6-bis(mercaptomethylthio)-1,3-dithiane, and 2-(2,2-bis(mercaptomethylthio)ethyl)-1,3-dithietane; and compounds represented by the following formula (2)

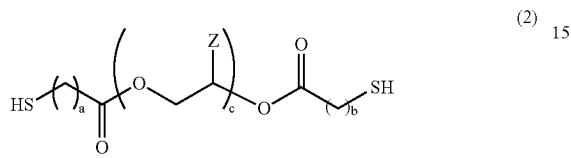

(2)

In the formula, a and b independently represent an integer of 1 to 4, and c represents an integer of 1 to 3. Z is hydrogen or a methyl group, and in a case in which a plurality of Zs is present, Zs may be identical or different, respectively, but the polythiol compound is not limited to the above-exemplified compounds. In the embodiment, a combination including at least one selected from the above-described polythiol compounds can be used.

Examples of the thiol compounds having a hydroxyl group include 2-mercaptoethanol, 3-mercapto-1,2-propanediol, glycerin bis(mercaptoacetate), 4-mercaptophenol, 2,3-dimercapto-1-propanol, pentaerythritol tris-(3-mercaptopropionate), pentaerythritol tris(thioglycolate), and the like, but the thiol compound is not limited to the above-exemplified compounds.

Furthermore, an oligomer of the above-described active hydrogen compound or a halogen substituent such as chlorine substituent or bromine substituent may be used. The active hydrogen compound can be singly used or a mixture of two or more active hydrogen compounds can be used.

As the thiourethane resin monomer, a polythiol compound is preferably used. For example, at least one selected from pentaerythritol tetrakis(2-mercaptoacetate), pentaerythritol tetrakis(3-mercaptopropionate), bis(mercaptoethyl)sulfide, 4-mercaptomethyl-1,8-dimercapto-3,6-dithiaoctane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, 2,5-dimercaptomrthyl-1,4-dithiane, 1,1,3,3-tetrakis(mercaptomethylthio)propane, 4,6-bis(mercaptomethylthio)-1,3-dithiane, 2-(2,2-bis(mercaptomethylthio)ethyl)-1,3-dithietane, trimethylolpropane tris(3-mercaptopropionate), and compounds of Formula (2) is preferably used, and at least one selected from pentaerythritol tetrakis(3-mercaptopropionate), 4-mercaptomethyl-1,8-dimercapto-3,6-dithiaoctane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, and compounds of Formula (2) is particularly preferably used.

In the embodiment, as the bi- or higher-functional active hydrogen compound (B), at least one selected from pentaerythritol tetrakis(3-mercaptopropionate), 4-mercaptomethyl-1,8-dimercapto-3,6-dithiaoctane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, the compounds of Formula (2), and trimethylolpropane tris(3-mercapto propionate) is particularly preferably used, and at least one selected from 4-mercaptomethyl-1,8-dimercapto-3,6-dithiaoctane and diethylene glycol bismercaptopropionate, which is a compound represented by Formula (2), is particularly preferably used.

[(C) Photochromic Compound]

In the embodiment, as the photochromic compound (C), a compound represented by the following formula (3) (hereinafter, also referred to as the compound (3)) can be used.

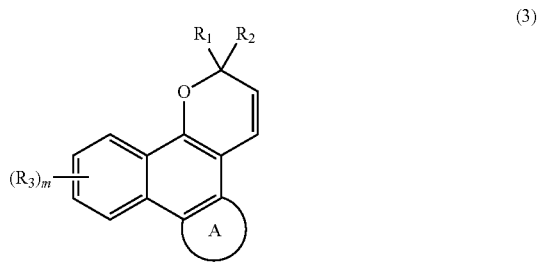

(3)

A first embodiment includes the following substituent.

In the formula, $R_1$ and $R_2$ may be identical or different, and independently represent a hydrogen atom;

a linear or branched alkyl group having 1 to 12 carbon atoms;

a cycloalkyl group having 3 to 12 carbon atoms;

a substituted or unsubstituted aryl group having 6 to 24 carbon atoms or a substituted or unsubstituted heteroaryl group having 4 to 24 carbon atoms; or an aralkyl or heteroaralkyl group (a linear or branched alkyl group having 1 to 4 carbon atoms that is substituted by the aryl group or heteroaryl group).

As the substituent for the substituted aryl group having 6 to 24 carbon atoms or the heteroaryl group having 4 to 24 carbon atoms, at least one is selected from a halogen atom, a hydroxyl group, a linear or branched alkyl group having 1 to 12 carbon atoms, a liner or branched alkoxy group having 1 to 12 carbon atoms, a linear or branched haloalkyl group having 1 to 12 carbon atoms that is substituted by at least one halogen atom, a linear or branched haloalkoxy group having 1 to 12 carbon atoms that is substituted by at least one halogen atom, a phenoxy group or naphthoxy group that is substituted by at least one linear or branched alkyl group or alkoxy group having 1 to 12 carbon atoms, a linear or branched alkenyl group having 2 to 12 carbon atoms, a —$NH_2$ group, a —NHR group, or a —$N(R_2)$ group (R represents a linear or branched alkyl group having 1 to 6 carbon atoms. In a case in which two Rs are present, the two Rs may be identical or different.) and a methacryloyl group or an acryloyl group.

$R_3$ may be identical or different, and independently represent a halogen atom;

a linear or branched alkyl group having 1 to 12 carbon atoms;

a cycloalkyl group having 3 to 12 carbon atoms;

a linear or branched alkoxy group having 1 to 12 carbon atoms;

a linear or branched haloalkyl group having 1 to 12 carbon atoms that is substituted by at least one halogen atom, a halocycloalkyl group having 3 to 12 carbon atoms that is substituted by at least one halogen atom, a linear or branched haloalkoxy group having 1 to 12 carbon atoms that is substituted by at least one halogen atom;

a substituted or unsubstituted aryl group having 6 to 24 carbon atoms or a substituted or unsubstituted heteroaryl group having 4 to 24 carbon atoms (as the substituent, including at least one selected from a halogen atom, a hydroxyl group, a linear or branched alkyl group having 1 to 12 carbon atoms, a linear or branched alkoxy group having 1 to 12 carbon atoms, a linear or branched haloalkyl group having 1 to 12 carbon atoms that is substituted by at least one halogen atom, a linear or branched haloalkoxy group having 1 to 12 carbon atoms that is substituted by at least one halogen atom, a phenoxy group or naphthoxy group substituted by at least one linear or branched alkyl group or alkoxy group having 1 to 12 carbon atoms, a linear or branched alkenyl group having 2 to 12 carbon atoms, and an amino group);

an aralkyl or heteroaralkyl group (a linear or branched alkyl group having 1 to 4 carbon atoms that is substituted by the aryl group or heteroaryl group);

a substituted or unsubstituted phenoxy or naphthoxy group (as the substituent, including at least one substituent selected from linear or branched alkyl groups or alkoxy groups having 1 to 6 carbon atoms);

—$NH_2$, —NHR, —$CONH_2$, or —CONHR (R represents a linear or branched alkyl group having 1 to 6 carbon atoms);

—$OCOR_8$ or —$COOR_8$ (here, $R_8$ represents a linear or branched alkyl group having 1 to 6 carbon atoms, a cycloalkyl group having 3 to 6 carbon atoms, or a phenyl group substituted by at least one substituents of the substituted aryl and the substituted heteroaryl group of $R_1$ or $R_2$, or an unsubstituted phenyl group).

One or more aromatic groups or non-aromatic groups can be formed by bonding at least two adjacent $R_a$s, and including a carbon atom bonding $R_3$. The aromatic groups or non-aromatic groups has one ring or two annelated rings containing a hetero atom selected from a group consisting of oxygen, sulfur, and nitrogen.

m is an integer of 0 to 4;

A represents the following formulae ($A_1$) to ($A_5$).

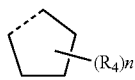

($A_1$)

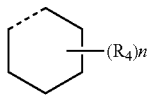

($A_2$)

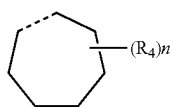

($A_3$)

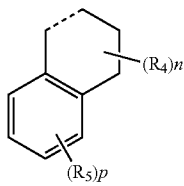

($A_4$)

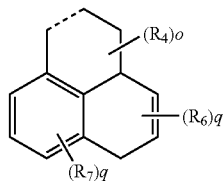

($A_5$)

In the annelated rings of ($A_1$) to ($A_5$), the dotted lines represent a chemical bond between a carbon $C_5$ and a carbon $C_6$ in a naphthopyran ring of a formula (3). The α bond in the annelated ring ($A_4$) or ($A_5$) is linked to the carbon $C_5$ or the carbon $C_6$ in the naphthopyran ring of Formula (3).

$R_4$ is identical or different, and independently represents OH, a linear or branched alkyl group or alkoxy group having 1 to 6 carbon atoms, or two $R_4$s form carbonyl (CO).

$R_5$, $R_6$, and $R_7$ independently represent a halogen atom (preferably fluorine, chlorine, or bromine);

a linear or branched alkyl group having 1 to 12 carbon atoms (preferably a linear or branched alkyl group having 1 to 6 carbon atoms);

a linear or branched haloalkyl group having 1 to 6 carbon atoms that is substituted by at least one halogen atom (preferably a fluoroalkyl group);

a cycloalkyl group having 3 to 12 carbon atoms;

a linear or branched alkoxy group having 1 to 6 carbon atoms;

a substituted or unsubstituted phenyl or benzyl group (as a substituent, in a case in which $R_1$ and $R_2$ in Formula (3) independently correspond to an aryl or heteroaryl group, including at least one substituent described in the definition of the $R_1$ and $R_2$ groups);

—$NH_2$, —NHR (here, R represents a linear or branched alkyl group having 1 to 6 carbon atoms);

a substituted or unsubstituted phenoxy group or naphthoxy group (as a substituent, including at least a linear or branched alkyl group or alkoxy group having 1 to 6 carbon atoms);

a —$COR_9$, —$COOR_8$, or —$CONHR_9$ group (here, $R_9$ represents a linear or branched alkyl group having 1 to 6 carbon atoms, a cycloalkyl group having 3 to 6 carbon atoms, or a substituted or unsubstituted phenyl or benzyl group (as a substituent, in a case in which $R_1$ and $R_2$ in Formula (3) independently correspond to an aryl or heteroaryl group, including at least one substituent described in the definition of the $R_1$ and $R_2$ groups)).

n is an integer of 0 to 6, o is an integer of 0 to 2, p is an integer of 0 to 4, and q is an integer of 0 to 3.

The photochromic compound (C) of Formula (3) possesses a high colourability, even at 40° C., combined with discoloration kinetics which is adapted to the applications sought after. The colors, which are easily accessible, vary from orange to blue.

In a second embodiment, A in the compound (3) can be the above-described annelated ring ($A_3$), ($A_4$) or ($A_5$).

Meanwhile, in the embodiment, examples of the photochromic compound also include a mixture of the compound (3) belonging to at least one different type selected from a group consisting of the compound (3) in which A=(A$_1$), the compound (3) in which A=(A$_2$), the compound (3) in which A=(A$_3$), the compound (3) in which A=(A$_4$), and the compound (3) in which A=(A$_5$).

The compound in a third embodiment is a compound of Formula (3) in which at least two adjacent R$_3$ groups form an aromatic group or a non-aromatic group. The aromatic group or non-aromatic group has one ring (for example, a phenyl group) or two annelated rings (for example, benzofuran groups) including at least one hetero atom selected from a group consisting of oxygen, sulfur, and nitrogen as necessary. The annelated ring is substituted by at least one substituent selected from the substituents in the aryl or heteroaryl group in R$_1$ and/or R$_2$ as necessary.

The family in the third embodiment includes, particularly, the compound (3) in which two adjacent R$_3$s form at least one annelated ring, for example, a benzo group, and in which at least one alicycle and/or aromatic ring A corresponding to (A$_1$), (A$_2$), (A$_3$), (A$_4$), or (A$_5$) is bonded to carbon atoms 5 and 6 of a phenanthrene skeleton.

The compound in the third embodiment is, particularly, naphthopyran (I) in which two adjacent R$_3$s format least one annelated ring, for example, a benzo group, and at least one substituted or unsubstituted alicycle and/or aromatic ring is coupled to carbon atoms 5 and 6 of the phenanthrene skeleton.

The compound in a fourth embodiment is the compound of Formula (3) excluding compounds in which A corresponds to (A$_1$) or (A$_2$) having at least one R$_4$ substituent that is different from hydrogen, in which at least two adjacent R$_3$s do not form at least one aromatic group or non-aromatic group. The aromatic group or non-aromatic group being excluded has one ring (for example, a phenyl group) or two annelated rings (for example, benzofuran groups) including at least one hetero atom selected from a group consisting of oxygen, sulfur, and nitrogen as necessary, and is substituted by at least one substituent selected from the substituents in the aryl or heteroaryl group in R$_1$ and/or R$_2$ as necessary.

The compound in the fourth embodiment is, particularly, naphthopyran (I) in which two adjacent R$_a$s do not form the annelated ring, for example, m=1 and R$_3$=—OMe, and the carbon atoms 5 and 6 in a naphthol skeleton are coupled to at least one alicycle A that is different from (A$_1$) and (A$_2$).

Preferably, the compound according to the embodiment is a compound in which, in Formula (3), R$_1$ and R$_2$ may be identical or different, and independently represent an aryl or heteroaryl group substituted as necessary in which the basic structure is selected from a group consisting of phenyl, naphthyl, biphenyl, pyridyl, furyl, benzofuryl, dibenzofuryl, N—(C$_1$-C$_6$)alkylcarbazole, thienyl, benzothienyl, dibenzothienyl, and julolidinyl group, R$_1$ and/or R$_2$ are preferably compounds representing a para-substituted phenyl group, or compounds in which R$_1$ and R$_2$ bond together so as to form an adamantyl or norbornyl group.

As the compound (3), it is possible to preferably use a compound represented by the following formula (4).

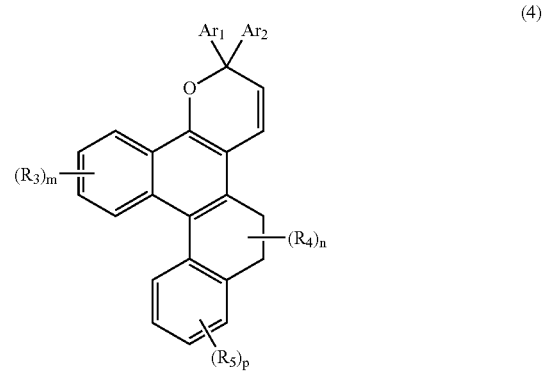

Ar$_1$ and Ar$_2$ are aromatic groups, may be identical or different, and exhibit a benzene ring or a thiophene ring that may be substituted. Examples of a substituent for the benzene ring or the thiophene ring include linear or branched alkyl groups having 1 to 10 carbon atoms, linear or branched alkoxy groups having 1 to 10 carbon atoms, and linear or branched alkyl mono (or di)-substituted amino group having 1 to 6 carbon atoms. R$_3$, R$_4$, R$_5$, m, n, and p have the same meaning as described above.

As the compound (3), a compound represented by the following formula (5) can be still more preferably used.

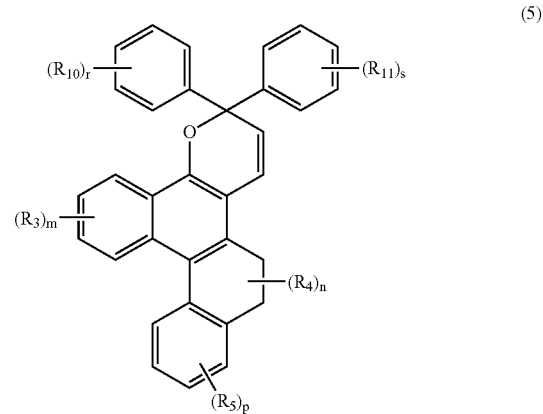

In Formula (5), R$_{10}$ and R$_{11}$ may be mutually identical or different, and represent a linear or branched alkyl group having 1 to 10 carbon atoms, a linear or branched alkoxy group having 1 to 10 carbon atoms, or a linear or branched alkyl mono (or di)-substituted amino group having 1 to 6 carbon atoms. When m is 2, adjacent R$_3$s bond together, and it is possible to form a ring structure by including a carbon atom to which R$_3$ is bonded. r and s are integers of 0 to 4. The ring structure is a substituted or unsubstituted aryl group having 6 to 24 carbon atoms or a substituted or unsubstituted heteroaryl group having 3 to 24 carbon atoms.

R$_3$, R$_4$, R$_5$, m, n, and p have the same meaning as described above.

Specific examples of the compound represented by Formula (5) include compounds represented by the following formula (6) or (7). In the invention, the compound represented by Formula (6) is preferred.

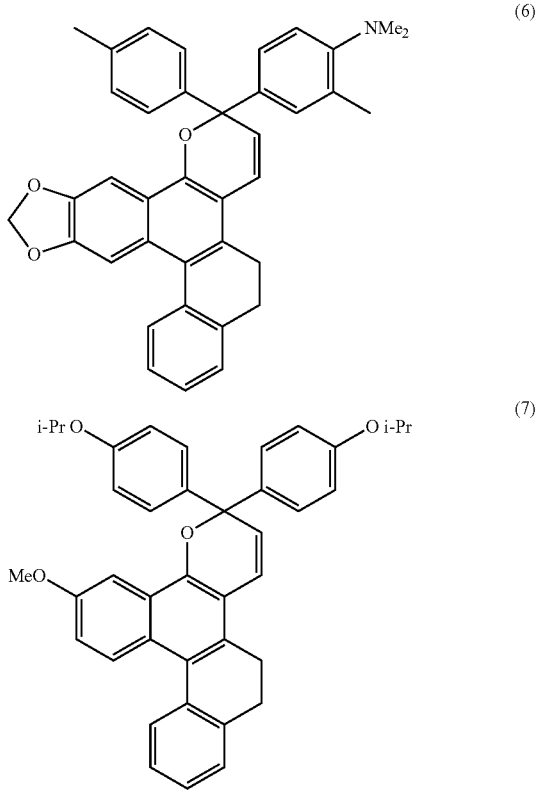

The compound represented by Formula (3), which is the photochromic compound (C), can be synthesized using a well-known method. For example, the compound can be synthesized using the method described in Japanese Unexamined Patent Application Publication No. 2004-500319.

[Other Components]

In addition to the isocyanate compounds (A), the active hydrogen compound (B), and the photochromic compound (C), the polymerizable composition may further include a polymerization catalyst, an internal mold release agent, a resin modifier, and the like.

Examples of the polymerization catalyst include tertiary amine compounds, inorganic or organic acid salt thereof, metal compounds, quaternary ammonium salts, and organic sulfonic acids.

As the internal mold release agent, an acidic phosphoric ester can be used. Examples of the acidic phosphoric ester include phosphoric acid monoesters, phosphoric acid diesters, and the like, the acidic phosphoric ester can be singly used, or a mixture of two or more acidic phosphoric esters can be used.

Examples of the resin modifier include episulfide compounds, alcohol compounds, amine compounds, epoxy compounds, organic acids, anhydrides thereof, olefin compounds including (meth) acrylate compounds, and the like.

<Process for Producing the Polymerizable Composition for an Optical Material>

The polymerizable composition for an optical material of the embodiment can be prepared by mixing the isocyanate compounds (A), the active hydrogen compound having two or more functional groups (B), and the photochromic compound (C) in one batch.

In the embodiment, the molar ratio of the mercapto group in the thiol compound to an isocyanato group in the isocyanate compound is in a range of 0.8 to 1.2, preferably in a range of 0.85 to 1.15, and more preferably in a range of 0.9 to 1.1. Within the above-described range, it is possible to obtain a resin that is preferably used as an optical material, particularly, an eyeglass plastic lens material.

In addition, the amount of the photochromic compound (C) being used can be set in a range of 10 ppm to 5000 ppm with respect to the total amount of the isocyanate compounds (A) and the active hydrogen compound (B).

In a case in which the polymerizable composition is prepared by mixing the isocyanate compounds (A), the active hydrogen compound (B), the photochromic compound (C), and other additives, the components are mixed at, generally, 25° C. or lower. There is a case in which a lower temperature is preferred from the viewpoint of the pot life of the polymerizable composition. However, in a case in which the solubility of the catalyst, the internal mold release agent, and the additives in a monomer is not favorable, it is also possible to dissolve the components in the monomer and the resin modifier by heating the components in advance.

In the embodiment, the method for manufacturing a resin molded product is not particularly limited, but a preferable manufacturing method is cast molding polymerization. First, the polymerizable composition is injected into a casting mold held using a gasket, tape, or the like. At this time, depending on the required properties of a plastic lens to be obtained, there are many cases in which it is preferable to carry out a degassing treatment under reduced pressure or a filtration treatment such as pressurization or depressurization.

Since the polymerization conditions are significantly changed depending on the composition of the polymerizable composition, the type or amount of the catalyst, the shape of the mold, and the like, the polymerization conditions are not limited, but the polymerization is carried out at a temperature in a range of approximately −50° C. to 150° C. for 1 to 50 hours. In some cases, it is preferable to hold or gradually heat the components in a temperature range of 10° C. to 150° C. and to cure the components for 1 hour to 25 hours.

If necessary, a treatment such as annealing may be carried out on the resin molded product. The treatment temperature is generally in a range of 50° C. to 150° C., preferably in a range of 90° C. to 140° C., and more preferably in a range of 100° C. to 130° C.

In the embodiment, when the resin is molded, similar to a well-known casting method, a variety of additives such as a chain extender, a crosslinking agent, a light stabilizer, an ultraviolet absorber, an antioxidant, a bluing agent, an oil-soluble dye, a filler, and an adhesion accelerator may be added depending on purposes in addition to the above-described "other components".

<Usage>

The thiourethane resin of the embodiment can be made into molded products having a variety of shapes by changing the types of the mold. The resin molded product has photochromic performance, has a high refractive index and high transparency, and can be used for a variety of optical materials such as a plastic lens. Particularly, the resin molded product can be preferably used as a plastic eyeglass lens.

[Plastic Eyeglass Lens]

A plastic eyeglass lens produced using the resin of the embodiment may be provided with a coating layer on a single surface or both surfaces as necessary.

The plastic eyeglass lens of the embodiment is comprised of a lens base material comprised of the above-described polymerizable composition and the coating layer.

Specific examples of the coating layer include a primer layer, a hard coat layer, an antireflection layer, anti-fog coating layer, an anti-fouling layer, a water-repellent layer, and the like. These coating layers can be singly used, or can be used in a multilayer form of a plurality of the coating layers. In a case in which the coating layers are provided on both surfaces, the same coating layers may be provided on both surfaces, and different coating layers may be provided on both surfaces.

The coating layer may include an ultraviolet absorbent for the purpose of protecting the lens or eyes from ultraviolet rays, an infrared absorbent for the purpose of protecting eyes from infrared rays, a light stabilizer or an antioxidant for the purpose of improving the weather resistance of the lens, a pigment or dye for the purpose of making the lens more stylish, furthermore, a photochromic pigment or a photochromic dye, an antistatic agent, and additionally, well-known additives for improving the performance of the lens. A layer coating the surface through application may include a variety of levelling agents for the purpose of improving the coating properties.

The primer layer is generally formed between the hard coat layer described below and the lens. The primer layer is a coating layer intended to improve the adhesiveness between the hard coat layer that are formed on the primer layer and the lens, and is capable of improving the impact resistance in some cases. Any materials can be used for the primer layer as long as the materials have strong adhesiveness to the obtained lens, and generally, an urethane-based resin, an epoxy-based resin, a polyester-based resin, a melanin-based resin, a primer composition mainly including polyvinyl acetal, or the like is used. The primer composition may include an appropriate solvent having no influence on the lens for the purpose of adjusting the viscosity of the composition. It is needless to say that the primer composition may not include a solvent.

The primer layer can be formed using any of a coating method and a dry method. In a case in which the coating method is used, the primer composition is applied to the lens using a well-known coating method such as spin coating or dip coating, and then is solidified, thereby forming the primer layer. In a case in which the dry method is used, the primer layer is formed using a well-known drying method such as a CVD method or a vacuum deposition method. When the primer layer is formed, a pretreatment such as an alkali treatment, a plasma treatment, or an ultraviolet treatment may be carried out on the surface of the lens as necessary for the purpose of improving the adhesiveness.

The hard coat layer is a coating layer intended to provide functions such as scratch resistance, abrasion resistance, moisture resistance, hot water resistance, heat resistance, weather resistance, and the like to the surface of the lens.

For the hard coat layer, generally, a hard coat composition including a curable organic silicon compound and one or more types of fine particles of oxides of elements selected from an element group of Si, Al, Sn, Sb, Ta, Ce, La, Fe, Zn, W, Zr, In, and Ti and/or one or more types of fine particles of a composite oxide of two or more elements selected from the above-described group.

The hard coat composition preferably includes, in addition to the above-described components, at least any of amines, amino acids, metal acetylacetonate complexes, organic acid metal salts, perchloric acids, perchloric acids, acids, metal chlorides, and multifunctional epoxy compounds. The hard coat composition may include an appropriate solvent having no influence on the lens, and may not include a solvent.

The hard coat layer can be formed by, generally, applying the hard coat composition using a well-known coating method such as spin coating or dip coating, and then is cured. Examples of a curing method include a curing method by thermal curing or the radiation of an energy ray such as an ultraviolet ray or a visible light ray. To suppress the occurrence of interference pattern, the refractive index of the hard coat layer preferably has a difference from the refractive index of the lens in a range of ±0.1.

Generally, the antireflection layer is formed on the hard coat layer as necessary. There are an inorganic antireflection layer and an organic antireflection layer, and in the case of the inorganic antireflection layer, the antireflection layer is formed using an inorganic oxide such as $SiO_2$ or $TiO_2$ and a drying method such as a vacuum deposition method, a sputtering method, an ion plating method, an ion beam assist method, or a CVD method. In the case of the organic antireflection layer, the antireflection layer is formed using a composition including an organic silicon compound and silica-based fine particles having inner cavities and a wet method.

There are a single-layered antireflection layer and a multi-layered antireflection layer, and in a case in which the single-layered antireflection layer is used, the refractive index is preferably lower than the refractive index of the hard coat layer by at least equal to or more than 0.1. To effectively develop the antireflection function, the antireflection layer is preferably a multi-layered antireflection layer, and in this case, a low-refractive index film and a high-refractive index film are alternately laminated. In this case as well, the refractive index difference between the low-refractive index film and the high-refractive index film is preferably equal to or more than 0.1. Examples of the high-refractive index film include $ZnO$, $TiO_2$, $CeO_2$, $Sb_2O_5$, $SnO_2$, $ZrO_2$, $Ta_2O_5$, and the like, and examples of the low-refractive index film include a $SiO_2$ film and the like.

An anti-fogging layer, an anti-fouling layer, and a water-repellent layer may be formed as necessary on the antireflection layer. Regarding a method for forming the anti-fogging layer, the anti-fouling layer, and the water-repellent layer, there is no particular limitation regarding the treatment method, the treatment material, and the like as long as no adverse influence is caused to the antireflection function, and well-known anti-fogging treatment methods, anti-fouling treatment method, water-repellent treatment methods, and materials can be used. Examples of the anti-fogging treatment method and the anti-fouling treatment method include a method of coating the surface with a surfactant, a method of adding a hydrophilic film to the surface so as to make the surface water-absorbable, a method of providing fine protrusions and recesses to the surface so as to make the surface water-absorbable, a method of making the surface water-absorbable using photocatalytic activity, a method of carrying out a highly water-repellent treatment so as to prevent the attachment of water droplets, and the like. In addition, examples of the water-repellent method include a method of forming a water-repellent treatment layer by depositing or sputtering a fluorine-containing silane compound or the like, a method of dissolving a fluorine-containing silane compound in a solvent, and then applying the solution, thereby forming a water-repellent treatment layer, and the like.

Priority is claimed based on Japanese Patent Application No. 2012-143125, filed on Jun. 26, 2012, the content of which is incorporated herein by reference.

EXAMPLES

Hereinafter, the invention will be described in more detail using examples, but the invention is not limited thereto.

A lens obtained through polymerization was evaluated by carrying out a performance test. In the performance test, the refractive index, Abbe number, heat resistance, specific gravity, and photochromic performance were evaluated using the following testing methods.

Refractive index (ne) and Abbe number (νe): measured at 20° C. using a PULFRICH refractometer KPR-30 manufactured by Shimadzu Corporation.

Heat resistance: the glass transition temperature (Tg) in the TMA penetration method (a load of 50 g and a pin point with 0.5 mmϕ) was measured as the heat resistance using a TMA-60 manufactured by Shimadzu Corporation.

Specific gravity: measured using an Archimedes method at 20° C.

Photochromic performance: a 2.0 mm-thick resin flat plate was produced, an ultraviolet ray of 365 nm was irradiated to the resin flat plate for 60 minutes from a location of a height of 155 mm using a Handy UV Lamp SLUV-6 manufactured by AS ONE Corporation, and the L* value, the a* value, and the b*value of the color of the resin flat plate after the UV radiation were measured using a chroma meter colorimeter (CR-200 manufactured by Konica Minolta). The change amount of the color was computed using the following equation on the basis of the L* value, the a* value, and the b*value after the UV radiation.

$$\Delta E^*ab = [(\Delta L^*)^2 + (\Delta a^*)^2 + (\Delta b^*)^2]^{1/2}$$

The computation result was evaluated using the following standards.

A lens having a ΔE*ab value of equal to or more than 10 was evaluated to be A, a lens having a ΔE*ab value in a range of equal to or more than 4 and less than 10 was evaluated to be B, and a lens having a ΔE*ab value of less than 4 was evaluated to be C.

Example 1

0.0375 g of dibutyl tin dichloride as a curing catalyst, 0.10 g of an internal mold release agent (trade name, ZELEC UN), and 0.050 g of a compound represented by Formula (6) as a photochromic pigment were mixed and dissolved at 15° C. in 50.57 g of 2,5(6)-bis(isocyanatomethyl)-bicyclo[2.2.1]heptane, thereby producing a homogeneous solution. 23.86 g of pentaerythritol tetrakis mercaptopropionate and 25.57 g of 4-mercaptomethyl-1,8-dimercapto-3,6-dithiaoctane were collectively added to the homogeneous solution, and the components were mixed and dissolved in a water bath at 15° C. for 30 minutes, thereby producing a homogeneous solution. The homogeneous solution was degassed at 600 Pa for one hour, then, was filtered using a 1 μm PTFE filter, and was incorporated into a mold set made up of a glass mold and tape. After the mold set was incorporated into an oven, the temperature was gradually increased from 25° C. to 120° C. for 20 hours, thereby polymerizing the solution. After the end of the polymerization, the mold set was removed from the oven, and the mold was removed, thereby obtaining a 2.0 mm-thick resin. The obtained resin flat plate was further annealed at 120° C. for four hours.

The performance test results of the obtained lenses are described in Table 1.

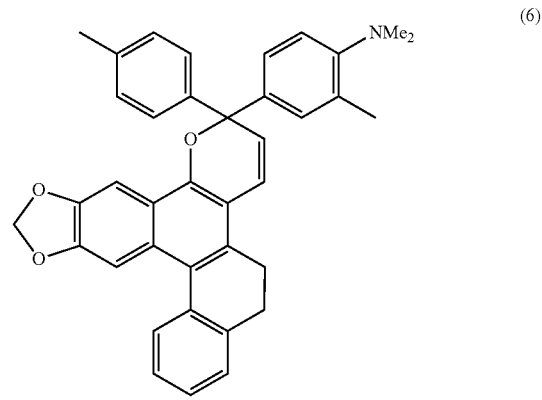 [SMILES: Cc1ccc(C2(c3ccc(N(C)C)c(C)c3)C=Cc3c4c(c5cc6c(cc5c3O2)OCO6)-c2ccccc2CC4)cc1]

(6)

Example 2

0.12 g of a mixture of triethylamine as a curing catalyst and an internal mold release agent (trade name, ZELEC UN), which is triethylamine:internal mold release agent=1:5.00, and 0.050 g of a compound represented by Formula (6) as a photochromic pigment were mixed and dissolved at 15° C. in 50.57 g of 2,5(6)-bis(isocyanatomethyl)-bicyclo[2.2.1]heptane, thereby producing a homogeneous solution. 23.86 g of pentaerythritol tetrakis mercaptopropionate and 25.57 g of 4-mercaptomethyl-1,8-dimercapto-3,6-dithiaoctane were collectively added to the homogeneous solution, and the components were mixed and dissolved in a water bath at 15° C. for 30 minutes, thereby producing a homogeneous solution. The homogeneous solution was degassed at 600 Pa for one hour, then, was filtered using a 1 μm PTFE filter, and was incorporated into a mold set made up of a glass mold and tape. After the mold set was incorporated into an oven, the temperature was gradually increased from 25° C. to 120° C. for 20 hours, thereby polymerizing the solution. After the end of the polymerization, the mold set was removed from the oven, and the mold was removed, thereby obtaining a 2.0 mm-thick resin. The obtained resin flat plate was further annealed at 120° C. for four hours.

The performance test results of the obtained lenses are described in Table 1.

Example 3

0.2500 g of dibutyl tin dichloride as a curing catalyst, 0.10 g of an internal mold release agent (trade name, ZELEC UN), and 0.050 g of a compound represented by Formula (6) as a photochromic pigment were mixed and dissolved at 15° C. in 58.65 g of bis(isocyanatocyclohexyl)methane, thereby producing a homogeneous solution. 4.11 g of diethylene glycol bis mercaptopropionate and 37.24 g of 4-mercaptomethyl-1,8-dimercapto-3,6-dithiaoctane were collectively added to the homogeneous solution, and the components were mixed and dissolved in a water bath at 15° C. for 30 minutes, thereby producing a homogeneous solution. The homogeneous solution was degassed at 600 Pa for one hour, then, was filtered using a 1 μm PTFE filter, and was incorporated into a mold set made up of a glass mold and tape. After the mold set was incorporated into an oven, the temperature was gradually increased from 25° C. to 120° C. for 20 hours, thereby polymerizing the solution. After the end of the polymerization, the mold set was removed from the oven, and the mold was removed, thereby obtaining a 2.0 mm-thick resin. The obtained resin flat plate was further annealed at 120° C. for four hours.

The performance test results of the obtained lenses are described in Table 1.

Example 4

0.18 g of a mixture of triethylamine as a curing catalyst and an internal mold release agent (trade name, ZELEC UN), which is triethylamine:internal mold release agent=1: 4.25, and 0.050 g of a compound represented by Formula (6) as a photochromic pigment were mixed and dissolved at 15° C. in 58.65 g of bis(isocyanatocyclohexyl)methane, thereby producing a homogeneous solution. 4.11 g of diethylene glycol bis mercaptopropionate and 37.24 g of 4-mercaptomethyl-1,8-dimercapto-3,6-dithiaoctane were collectively added to the homogeneous solution, and the components were mixed and dissolved in a water bath at 15° C. for 30 minutes, thereby producing a homogeneous solution. The homogeneous solution was degassed at 600 Pa for one hour, then, was filtered using a 1 μm PTFE filter, and was incorporated into a mold set made up of a glass mold and tape. After the mold set was incorporated into an oven, the temperature was gradually increased from 25° C. to 120° C. for 20 hours, thereby polymerizing the solution. After the end of the polymerization, the mold set was removed from the oven, and the mold was removed, thereby obtaining a 2.0 mm-thick resin. The obtained resin flat plate was further annealed at 120° C. for four hours.

The performance test results of the obtained lenses are described in Table 1.

Example 5

1.759 g of an internal mold release agent (trade name, ZELEC UN) and 0.050 g of a compound represented by Formula (6) as a photochromic pigment were mixed and dissolved at 40° C. in 60.10 g of RAVolution™ IS manufactured by ACOMON AG, thereby producing a homogeneous solution. 39.90 g of RAVolution™ PO manufactured by ACOMON AG were collectively added to the homogeneous solution, and the components were mixed and dissolved in a water bath at 40° C. for 30 minutes, thereby producing a homogeneous solution. The homogeneous solution was degassed at 600 Pa for one hour, then, was filtered using a 1 μm PTFE filter, and was incorporated into a mold set made up of a glass mold and tape. After the mold set was incorporated into an oven, the temperature was gradually increased from 40° C. to 130° C. for 20 hours, thereby polymerizing the solution. After the end of the polymerization, the mold set was removed from the oven, and the mold was removed, thereby obtaining a 2.0 mm-thick resin. The obtained resin flat plate was further annealed at 120° C. for four hours.

The performance test results of the obtained lenses are described in Table 1.

Example 6

0.0350 g of dibutyl tin dichloride as a curing catalyst, 0.10 g of an internal mold release agent (trade name, ZELEC UN), and 0.050 g of a compound represented by Formula (6) as a photochromic pigment were mixed and dissolved at 15° C. in 37.89 g of 1,6-hexamethylene diisocyanate, thereby producing a homogeneous solution. 62.11 g of trimethylolpropane tris(3-mercaptopropionate) was added to the homogeneous solution, and the components were mixed and dissolved in a water bath at 15° C. for 30 minutes, thereby producing a homogeneous solution. The homogeneous solution was degassed at 600 Pa for one hour, then, was filtered using a 1 μm PTFE filter, and was incorporated into a mold set made up of a glass mold and tape. After the mold set was incorporated into an oven, the temperature was gradually increased from 25° C. to 120° C. for 20 hours, thereby polymerizing the solution. After the end of the polymerization, the mold set was removed from the oven, and the mold was removed, thereby obtaining a 2.0 mm-thick resin. The obtained resin flat plate was further annealed at 120° C. for four hours.

The performance test results of the obtained lenses are described in Table 1.

Example 7

0.2500 g of dibutyl tin dichloride as a curing catalyst, 0.10 g of an internal mold release agent (trade name, ZELEC UN), and 0.050 g of a compound represented by Formula (6) as a photochromic pigment were mixed and dissolved at 15° C. in 54.58 g of isophorone diisocyanate, thereby producing a homogeneous solution. 4.51 g of diethylene glycol bis mercaptopropionate and 40.91 g of 4-mercaptomethyl-1,8-dimercapto-3,6-dithiaoctane were collectively added to the homogeneous solution, and the components were mixed and dissolved in a water bath at 15° C. for 30 minutes, thereby producing a homogeneous solution. The homogeneous solution was degassed at 600 Pa for one hour, then, was filtered using a 1 μm PTFE filter, and was incorporated into a mold set made up of a glass mold and tape. After the mold set was incorporated into an oven, the temperature was gradually increased from 25° C. to 120° C. for 20 hours, thereby polymerizing the solution. After the end of the polymerization, the mold set was removed from the oven, and the mold was removed, thereby obtaining a 2.0 mm-thick resin. The obtained resin flat plate was further annealed at 120° C. for four hours.

The performance test results of the obtained lenses are described in Table 1.

Example 8

0.2500 g of dibutyl tin dichloride as a curing catalyst, 0.10 g of an internal mold release agent (trade name, ZELEC UN), and 0.050 g of a compound represented by Formula (6) as a photochromic pigment were mixed and dissolved at 15° C. in 59.40 g of bis(isocyanatocyclohexyl) methane, thereby producing a homogeneous solution. 40.60 g of 4-mercaptomethyl-1,8-dimercapto-3,6-dithiaoctane was added to the homogeneous solution, and the components were mixed and dissolved in a water bath at 15° C. for 30 minutes, thereby producing a homogeneous solution. The homogeneous solution was degassed at 600 Pa for one hour, then, was filtered using a 1 μm PTFE filter, and was incorporated into a mold set made up of a glass mold and tape. After the mold set was incorporated into an oven, the temperature was gradually increased from 25° C. to 120° C. for 20 hours, thereby polymerizing the solution. After the end of the polymerization, the mold set was removed from the oven, and the mold was removed, thereby obtaining a 2.0 mm-thick resin. The obtained resin flat plate was further annealed at 120° C. for four hours.

The performance test results of the obtained lenses are described in Table 1.

Comparative Example 1

0.0100 g of dibutyl tin dichloride as a curing catalyst, 0.10 g of an internal mold release agent (trade name, ZELEC UN), and 0.050 g of a compound represented by Formula (6) as a photochromic pigment were mixed and dissolved at 15° C. in 50.71 g of m-xylylene diisocyanate, thereby producing a homogeneous solution. 49.29 g of a mixture of 5,7-dimercaptomethyl-1,11-dimercapto-3,6,9-trithiaundecane, 4,7-dimercaptomethyl-1,11-dimercapto-3,6,9-trithiaundecane, and 4,8-dimercaptomethyl-1,11-dimercapto-3,6,9-trithiaundecane was added to the homogeneous solution, and the components were mixed and dissolved in a water bath at 15° C. for 30 minutes, thereby producing a homogeneous solution. The homogeneous solution was degassed at 600 Pa for one hour, then, was filtered using a 1 μm PTFE filter, and was incorporated into a mold set made up of a glass mold and tape. After the mold set was incorporated into an oven, the temperature was gradually increased from 25° C. to 120° C. for 20 hours, thereby polymerizing the solution. After the end of the polymerization, the mold set was removed from the oven, and the mold was removed, thereby obtaining a 2.0 mm-thick resin. The obtained resin flat plate was further annealed at 120° C. for four hours.

The performance test results of the obtained lenses are described in Table 1.

Comparative Example 2

0.0300 g of dibutyl tin dichloride as a curing catalyst, 0.10 g of an internal mold release agent (trade name, ZELEC UN), and 0.050 g of a compound represented by Formula (6) as a photochromic pigment were mixed and dissolved at 15° C. in 48.50 g of tolylene diisocyanate, thereby producing a homogeneous solution. 5.12 g of diethylene glycol bis mercaptopropionate and 46.38 g of 4-mercaptomethyl-1,8-dimercapto-3,6-dithiaoctane were collectively added to the homogeneous solution, and the components were mixed and dissolved in a water bath at 15° C. for 30 minutes, thereby producing a homogeneous solution. The homogeneous solution was degassed at 600 Pa for one hour, then, was filtered using a 1 μm PTFE filter, and was incorporated into a mold set made up of a glass mold and tape. After the mold set was incorporated into an oven, the temperature was gradually increased from 25° C. to 120° C. for 20 hours, thereby polymerizing the solution. After the end of the polymerization, the mold set was removed from the oven, and the mold was removed, thereby obtaining a 2.0 mm-thick resin. The obtained resin flat plate was further annealed at 120° C. for four hours.

The performance test results of the obtained lenses are described in Table 1.

Comparative Example 3

0.0300 g of dibutyl tin dichloride as a curing catalyst, 0.10 g of an internal mold release agent (trade name, ZELEC UN), and 0.050 g of a compound represented by Formula (6) as a photochromic pigment were mixed and dissolved at 15° C. in 49.26 g of tolylene diisocyanate, thereby producing a homogeneous solution. 50.74 g of 4-mercaptomethyl-1,8-dimercapto-3,6-dithiaoctane was added to the homogeneous solution, and the components were mixed and dissolved in a water bath at 15° C. for 30 minutes, thereby producing a homogeneous solution. The homogeneous solution was degassed at 600 Pa for one hour, then, was filtered using a 1 μm PTFE filter, and was incorporated into a mold set made up of a glass mold and tape. After the mold set was incorporated into an oven, the temperature was gradually increased from 25° C. to 120° C. for 20 hours, thereby polymerizing the solution. After the end of the polymerization, the mold set was removed from the oven, and the mold was removed, thereby obtaining a 2.0 mm-thick resin. The obtained resin flat plate was further annealed at 120° C. for four hours.

The performance test results of the obtained lenses are described in Table 1.

TABLE 1

| | Monomer configuration | | | Resin properties | | | | Photochromic performance | |
| | Isocyanate | Poly(ti)ol | | Refractive index [ne] | Abbe number [ve] | Heat resistance [° C.] | Specific gravity | Change amount of hue | Evaluation |
|---|---|---|---|---|---|---|---|---|---|
| Example 1 | (A)-1 | (B)-1 | (B)-2 | 1.598 | 40 | 118 | 1.30 | 4.36 | B |
| Example 2 | (A)-1 | (B)-1 | (B)-2 | 1.598 | 40 | 118 | 1.30 | 5.26 | B |
| Example 3 | (A)-3 | (B)-2 | (B)-4 | 1.596 | 40 | 123 | 1.23 | 12.48 | A |
| Example 4 | (A)-3 | (B)-2 | (B)-4 | 1.596 | 40 | 123 | 1.23 | 11.25 | A |
| Example 5 | (A)-4 | (B)-5 | — | 1.509 | 54 | 94 | 1.11 | 15.46 | A |
| Example 6 | (A)-5 | (B)-6 | — | 1.555 | 43 | 57 | 1.26 | 4.31 | B |
| Example 7 | (A)-6 | (B)-2 | (B)-4 | 1.596 | 40 | 125 | 1.24 | 6.72 | B |
| Example 8 | (A)-3 | (B)-2 | — | 1.600 | 39 | 126 | 1.23 | 11.09 | A |
| Comparative Example 1 | (A)-2 | (B)-3 | — | 1.668 | 32 | 103 | 1.37 | 1.92 | C |
| Comparative Example 2 | (A)-7 | (B)-2 | (B)-4 | 1.680 | 26 | 130 | 1.38 | 3.30 | C |
| Comparative Example 3 | (A)-7 | (B)-2 | — | 1.688 | 25 | 143 | 1.38 | 3.65 | C |

Reference signs in Table 1 represent the following contents.

(A)-1: 2,5(6)-bis(isocyanatomethyl)-bicyclo[2,2,1]heptane

Meanwhile, in each of the above-described examples, as 2,5(6)-bis(isocyanatomethyl)-bicyclo[2.2.1]heptane, a mixture of 2,5-bis(isocyanatomethyl)-bicyclo[2,2,1]heptane and 2,6-bis(iscyanatomethyl)-bicyclo[2,2,1]heptane was used.

(A)-2: m-xylylene diisocyanate (A)-3: bis(isocyanatocyclohexyl)methane (A)-4: RAVolution™ IS (alicyclic isocyanate) manufactured by Acomon AG (A)-5: 1,6-Hexamethylene diisocyanate (A)-6: Isophorone diisocyanate (A)-7: Tolylene diisocyanate (B)-1: Pentaerythritol tetrakis mercaptopropionate (B)-2: 4-Mercapto-1,8-dimercapto-3,6-dithiaoctane (B)-3: A mixture of 5,7-dimercaptomethyl-1,11-dimercapto-3,6,9-trithiaundecane, 4,7-dimercaptomethyl-1,11-dimercapto-3,6,9-trithiaundecane, and 4,8-dimercaptomethyl-1,11-dimercapto-3,6,9-trithiaundecane (B)-4: Diethylene glycol bismercaptopropionate (B)-5: RAVolution™ PO (polyol (mixture)) manufactured by Acomon AG (B)-6: trimethylol propane tris(3-mercaptopropionate)

From the above-described results, it was found that, in the resins of the examples obtained using the aliphatic isocyanate or the alicyclic isocyanate, a desired photochromic performance was confirmed; however, in the resins of the comparative examples obtained using m-xylylene diisocyanate or trilene diisocyanate that is an isocyanate having an aromatic ring, a desired photochromic performance could not be obtained.

The invention claimed is:

1. A polymerizable composition for an optical material comprising:

(A) one or more isocyanate compounds selected from aliphatic isocyanate compounds and alicyclic isocyanate compounds;

(B) an active hydrogen compound having two or more functional groups; and (C) a photochromic compound, wherein the isocyanate compound (A) is one or more selected from the group consisting of 1,6-hexamethylene diisocyanate, 2,5-bis(isocyanatomethyl)bicyclo-[2.2.1]-heptane, 2,6-bis(isocyanatomethyl)bicyclo-[2.2.1]-heptane, isophorone diisocyanate, and compounds represented by the following formula (1)

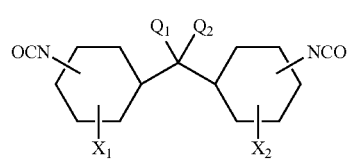

wherein in the formula (1), $Q_1$ and $Q_2$ may be identical or different and represent a hydrogen atom or an alkyl group having 1 to 6 carbon atoms; and $X_1$ and $X_2$ may be identical or different and represent a hydrogen atom or an alkyl group having 1 to 6 carbon atoms, and wherein the photochromic compound (C) is represented by the following formula

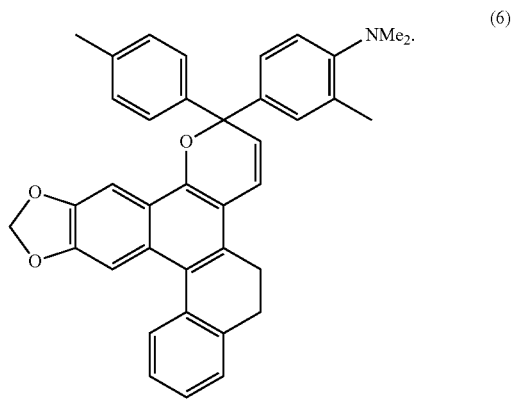 [SMILES: Cc1ccc(C2(c3ccc(N(C)C)c(C)c3)C=Cc3c4c(c5cc6c(cc5c3O2)OCO6)-c2ccccc2CC4)cc1]

2. The polymerizable composition for an optical material according to claim 1,
wherein the isocyanate compound (A) includes the compounds represented by Formula (1).

3. The polymerizable composition for an optical material according to claim 1,
wherein the alicyclic isocyanate compound is bis(isocyanatocyclohexyl)methane.

4. The polymerizable composition for an optical material according to claim 1,
wherein the active hydrogen compound (B) is one or more selected from the group consisting of polyol compounds, polythiol compounds, and thiol compounds having a hydroxyl group.

5. The polymerizable composition for an optical material according to claim 1,
wherein the active hydrogen compound (B) is one or more selected from the group consisting of pentaerythritol tetrakis(2-mercaptoacetate), pentaerythritol tetrakis(3-mercaptopropionate), bis(mercaptoethyl) sulfide, 4-mercaptomethyl-1,8-dimercapto-3,6-dithiaoctane, 5,7-dimercaptomethyl-1,11-dimercapto-3,6,9-trithiaundecane, 4,7-dimercaptomethyl-1,11-dimercapto-3,6,9-trithiaundecane, 4,8-dimercaptomethyl-1,11-dimercapto-3,6,9-trithiaundecane, 2,5-dimercapto-1,4-dithiane, 1,1,3,3-tetrakis(mercaptomethylthio) propane, 4,6-bis(mercaptomethylthio)-1,3-dithiane, 2-(2,2-bis(mercaptomethylthio)ethyl)-1,3-dithietane, trimethylolpropane tris(3-mercaptopropionate), and compounds represented by Formula (2)

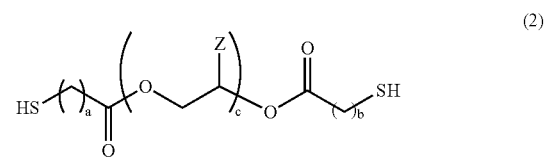

wherein a and b independently represent an integer of 1 to 4, and c represents an integer of 1 to 3; Z is hydrogen or a methyl group, and in the case in which a plurality of Zs are present, they may be identical or different.

6. An optical material comprised of the polymerizable composition according to claim 1.

7. A plastic lens including a base material comprised of the polymerizable composition according to claim 1.

8. A method for manufacturing a plastic lens comprising:
a step of mixing (A) one or more isocyanate compounds selected from aliphatic isocyanate compounds and alicyclic isocyanate compounds, (B) an active hydrogen compound having two or more functional groups, and (C) a photochromic compound in one batch to prepare a polymerizable composition for an optical material; and
a step of forming a lens base material by polymerizing the polymerizable composition in a mold,
wherein the isocyanate compound (A) is one or more selected from the group consisting of 1,6-hexamethylene diisocyanate, 2,5-bis(isocyanatomethyl)bicyclo-[2.2.1]-heptane, 2,6-bis(isocyanatomethyl)bicyclo-[2.2.1]-heptane, isophorone diisocyanate, and compounds represented by the following formula (1)

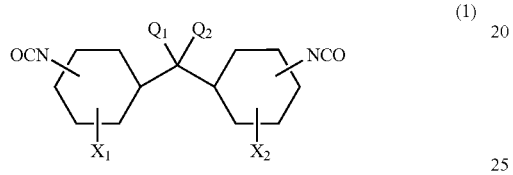
(1)

wherein in the formula (1), $Q_1$ and $Q_2$ may be identical or different and represent a hydrogen atom or an alkyl group having 1 to 6 carbon atoms; and $X_1$ and $X_2$ may be identical or different and represent a hydrogen atom or an alkyl group having 1 to 6 carbon atoms, and
wherein the photochromic compound (C) is represented by the following formula (6),

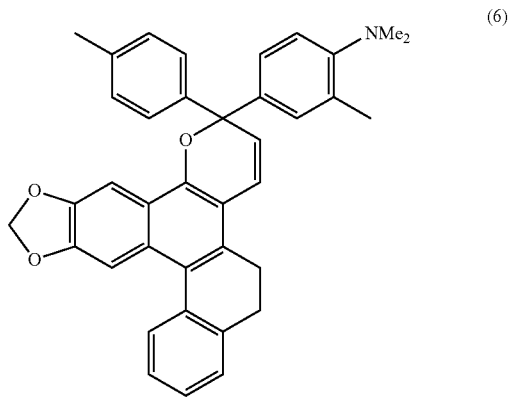 [SMILES: Cc1ccc(C2(c3ccc(N(C)C)c(C)c3)C=Cc3c4c(c5cc6c(cc5c3O2)OCO6)-c2ccccc2CC4)cc1]
(6)

* * * * *